(12) United States Patent
Bossier et al.

(10) Patent No.: US 10,304,322 B2
(45) Date of Patent: May 28, 2019

(54) REMOTE CONTROL SYSTEM FOR MEDICAL APPARATUS

(71) Applicant: Ion Beam Applications, Louvain-la-Neuve (BE)

(72) Inventors: Vincent Bossier, Saint Gilles (BE); David Wikler, Waterloo (BE); Frédéric Genin, Ottignies (BE); Sofie Gillis, Herne (BE); Christophe Bauvir, Rhisnes (BE); Henri Bourmorck, Corroy-le-Château (BE); Geoffroy Herbin, Brussels (BE); Olivier Scalbert, Brussels (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 412 days.

(21) Appl. No.: 15/008,294

(22) Filed: Jan. 27, 2016

(65) Prior Publication Data

US 2016/0217684 A1 Jul. 28, 2016

(30) Foreign Application Priority Data

Jan. 27, 2015 (EP) .................................... 15152723

(51) Int. Cl.
*G08C 17/02* (2006.01)
*A61B 6/00* (2006.01)
*A61N 5/10* (2006.01)

(52) U.S. Cl.
CPC .............. *G08C 17/02* (2013.01); *A61B 6/548* (2013.01); *A61N 5/1048* (2013.01); *A61N 2005/1074* (2013.01); *G08C 2201/50* (2013.01); *G08C 2201/60* (2013.01); *G08C 2201/70* (2013.01)

(58) Field of Classification Search
CPC ................ G08C 17/02; G08C 2201/60; G08C 2201/50; G08C 2201/70; A61B 6/548; A61N 5/1048; A61N 2005/1074
See application file for complete search history.

(56) References Cited

U.S. PATENT DOCUMENTS

| 6,657,743 | B1 * | 12/2003 | Otsuka | .................. | H04L 51/066 |
| | | | | | 358/1.15 |
| 8,657,743 | B2 | 2/2014 | Rietzel et al. | | |
| 2002/0070866 | A1 * | 6/2002 | Newham | ................ | A61B 5/1115 |
| | | | | | 340/573.1 |

(Continued)

*Primary Examiner* — Thomas D Alunkal
(74) *Attorney, Agent, or Firm* — Finnegan, Henderson, Farabow, Garrett & Dunner LLP (57) ABSTRACT

An apparatus comprising a wireless communication device for enabling the remote control of a medical apparatus The apparatus includes a remote control enable device comprising a transmitter and one or more switches, actuatable by enable buttons. The buttons allow an operator to close the switch(es), causing the transmitter to send a status signal related to the status (open or closed) of the switch(es), to a receiver configured to communicate said status signal to a control unit. The control unit verifies the signal on a number of criteria. When all required criteria have been met, remote control of the medical apparatus is allowed. In an embodiment the remote control enable device is configured to maintain the power supply to a transmitting chip sufficiently long, upon opening a switch, so that a check can be performed on the correct functioning of the switch after the switch has been opened.

19 Claims, 10 Drawing Sheets

(56) References Cited

U.S. PATENT DOCUMENTS

| | | | |
|---|---|---|---|
| 2003/0130835 A1* | 7/2003 | Azzam | G06F 17/278 |
| | | | 704/1 |
| 2005/0004630 A1* | 1/2005 | Kagermeier | A61B 5/0002 |
| | | | 607/60 |
| 2007/0075856 A1* | 4/2007 | Wu | G06F 21/88 |
| | | | 340/541 |
| 2008/0130835 A1 | 6/2008 | Peterson et al. | |
| 2011/0279276 A1* | 11/2011 | Newham | A61B 5/115 |
| | | | 340/573.4 |
| 2012/0191162 A1* | 7/2012 | Villa | A61N 5/06 |
| | | | 607/89 |

* cited by examiner

REMOTE CONTROL SYSTEM FOR MEDICAL APPARATUS

CROSS-REFERENCE TO RELATED APPLICATION

This U.S. patent application claims priority under 35 U.S.C. § 119 to European Patent Application No. EP 15152723.1, filed Jan. 27, 2015. The aforementioned application is incorporated herein by reference in its entirety.

TECHNICAL FIELD

Embodiments of the present disclosure relate to the remote control of a medical apparatus such as a moving gantry in a radiation therapy treatment room.

BACKGROUND

Remote control of medical equipment is known in the art. For reasons of safety, verification procedures are required to ensure that a remote control device is correctly communicating with a medical apparatus. In the case of multiple remote controls being used in the same environment, for example to control multiple items of medical equipment, identification protocols avoid a remote control being inadvertently connected to the wrong medical apparatus.

In the area of radiation/particle therapy treatment, remote control of medical equipment has also been described, for example in U.S. Pat. No. 8,657,743, where the remote control of certain processes is enabled by placing the remote control device in a pre-defined location. This is, however, a cumbersome procedure and includes a variety of drawbacks. For example, it makes it difficult to react quickly in an emergency, and can reduce the degree of efficiency of the control process by making the process possible only from a given location. There is a need for improvements to existing systems in terms of safety and efficiency of use.

SUMMARY

Embodiments of the present disclosure may provide improvements over existing remote control systems. Embodiments of the present disclosure are related to an apparatus and method for controlling a medical apparatus.

Embodiments of the present disclosure relate to an apparatus for controlling one or more operations of a medical apparatus, comprising:
  a remote control device configured to control said one or more operations of said medical apparatus through a first wireless communication channel,
  a remote control enable device comprising:
    one or more manually operable switches,
    a wireless transmitter configured to transmit, through a second wireless communication channel, a status signal related at least to the status of said one or more switches,
  a receiving device configured to receive said status signal,
  a control unit coupled to the receiving device, and configured to allow said one or more operations when said switch is closed or, in the case of multiple switches, when said switches are closed simultaneously,
  wherein the remote control device and the remote control enable device are incorporated in a common hand-held housing including one or more buttons configured to operate said one or more switches.

According to an embodiment, said remote control enable device may comprise a power source and circuitry configured to power said wireless transmitter, and further configured such that the transmitter is powered only when said switch is closed or, in the case of multiple switches, when said switches are closed simultaneously.

According to an embodiment, said circuitry may comprise one or more components configured to maintain a power supply to the wireless transmitter that is sufficient for enabling transmission, during a timeframe after opening one of said switches, said timeframe being sufficiently long for the transmitter to transmit one or more status signals during said timeframe, and wherein the control unit is configured to check the correct functioning of the opened switch based on the status signals transmitted during said timeframe.

According to an embodiment, the wireless transmitter may be a wireless communication chip comprising power supply pins, wherein one or more components configured to maintain the power supply may comprise a capacitor coupled between the power supply pins of the chip.

According to an embodiment, the circuitry may further comprise a delay circuit coupled to at least one of said switches, said delay circuit being configured to force, upon opening the switch, the output terminal of the switch to zero according to a delayed characteristic as compared to the case where no delay circuit is present.

According to an embodiment the apparatus of the present disclosure may comprise a connection between the remote control enable device and the remote control device, wherein the remote control enable device is further equipped with circuitry for detecting information on the status of the switch or switches and transmitting said information through said connection to the remote control device, and wherein the remote control device is configured to communicate said information to the control unit, through the first wireless communication channel.

According to an embodiment, the remote control enable device may comprise two switches, and said information on the status of the switches specifies whether or not one switch is open while the other is closed.

According to an embodiment, said remote control enable device and/or said remote control device may be configured to be removed and re-inserted in the housing.

According to an embodiment, the remote control device may comprise a mobile phone that is mounted in said housing, and that is equipped with a control program allowing the control of said medical apparatus.

According to an embodiment, the present disclosure relates to a hand-held device comprising a housing, a remote control enable device and a remote control device configured to be used in the apparatus according to any of the embodiments.

According to an embodiment, the present disclosure relates to a method for controlling a medical apparatus by an operator, using an apparatus according to any of the previous embodiments, the method comprising the steps of:
  closing, simultaneously, on or more switches on the remote control enable device,
  sending, by the remote control enable device, a status signal to a receiving device configured to communicate the signal to a control unit, wherein the status signal is associated with at least the status of the one or more switches,
  determining that the status signal meets one or more criteria, wherein the one or more criteria comprise whether the one or more switches are closed, enabling, by the control unit, the operator to control the operation of the medical apparatus based on the determination, operating the medical apparatus using the remote control device.

According to an embodiment, the present disclosure relates to an apparatus for controlling one or more operations of a medical apparatus, comprising:

a remote control device configured to control said one or more operations of said medical apparatus through a first communication channel, a remote control enable device comprising:
one or more switches,
a wireless transmitter configured to transmit, through a second, wireless communication channel, a status signal related at least to the status of said one or more switches, a receiving device configured to receive said status signal, a control unit coupled to the receiving device, and configured to allow said one or more operations when said one or more switches are closed simultaneously, wherein said remote control enable device comprises a power source and circuitry configured to power said wireless transmitter, and further configured such that the transmitter is powered only when said one or more switches are dosed simultaneously, and wherein said circuitry comprises one or more components configured to maintain a power supply to the wireless transmitter that is sufficient for enabling transmission, during a timeframe after the opening of one of said switches, said timeframe being sufficiently long for the transmission means to transmit one or more status signals during said timeframe, and wherein the control unit is configured to check the correct functioning of the opened switch based on the status signals transmitted during said timeframe.

According to an embodiment, the wireless transmitter may be a wireless communication chip comprising power supply pins, and said one or more components configured to maintain the power comprise a capacitor coupled between the power supply pins of the chip.

According to an embodiment, the circuitry may further comprise a delay circuit coupled to at least one of said switches, said delay circuit being configured to force, upon opening the switch, the output terminal of the switch to zero according to a delayed characteristic as compared to the case where no delay circuit is present.

DETAILED DESCRIPTION

The present disclosure relates to an apparatus for remote control of a medical apparatus, comprising a wireless communication device for enabling said remote control. The device may hereafter be referred to as a "remote control enable device" or "RC enable device." The RC enable device of the present disclosure is distinct from the wireless remote control device as will be explained in further detail below. According to an embodiment, the RC enable device is incorporated together with a wireless remote control device in a common hand-held housing. Both the RC enable device and the remote control device are operated manually by the operator. The remote control device may not be used to control the medical apparatus unless the remote control enable device is actuated, in the manner described below. The incorporation of these two devices in a common hand-held housing increases the efficiency of use of the remote control, whilst ensuring a high level of safety. In the area of particle therapy equipment, e.g. equipment for controlling the movement of a rotating gantry, the present disclosure therefore provides a significant improvement over existing systems.

The RC enable device comprises a transmitter and one or more switches, actuatable by enable buttons. The buttons allow an operator to close the switch(es), which causes the sending by the transmitter of a status signal, i.e. a signal related to the status (open or closed) of the switch or switches, to a receiver that is configured to communicate said status signal to a control unit. The control unit verifies the signal on a number of criteria. When all required criteria have been met, remote control of the medical apparatus is allowed, said remote control being executed from a remote control device incorporated in the same hand-held housing as the RC enable device. When one or more of the criteria is not met, operation of the medical apparatus by the remote control is denied. The remote control device communicates with the medical apparatus and the control unit over a communication channel that may be different from the wireless communication channel used between the RC enable device and the control unit. The RC enable device and the remote control device may therefore have their own dedicated transmitting means, configured to transmit respectively to their own dedicated receiving means. The remote control enable device and the remote control device may therefore be physically separate devices, wherein one or both may be removable from the common housing. In embodiments, a cable connection may be present between the two device.

Figure 1:
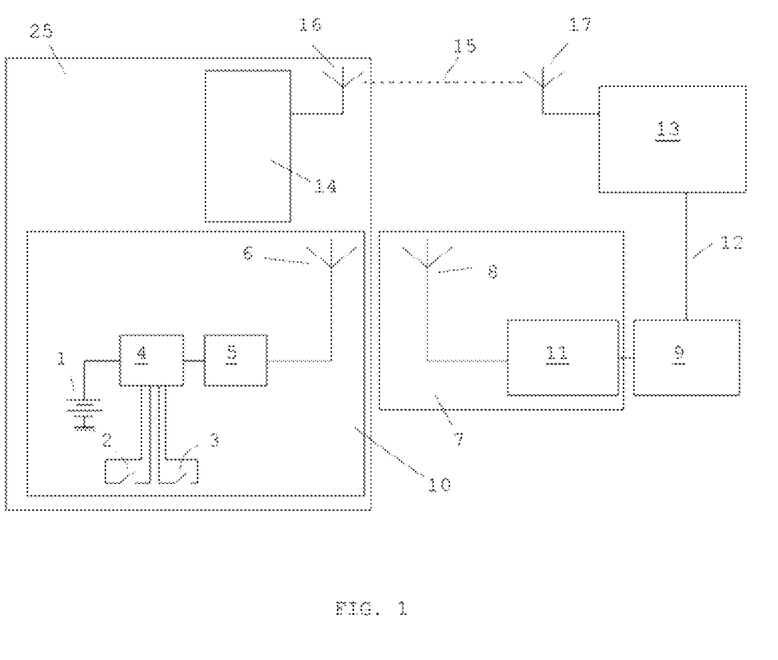
FIG. 1 illustrates an exemplary apparatus according to the present disclosure.

FIG. 1 illustrates an apparatus according to an embodiment. The RC enable device 10 comprises a power source 1 (note that the ground symbol used does not imply that the source must be grounded at all times, as a battery source may be used), two switches 2 and 3, each switch being operable by a respective RC enable button (not shown), circuitry 4 for producing a signal that translates the state of the two switches into an activation signal, a wireless transmission device 5 configured to produce, upon receiving the activation signal, a status signal, the content of which is related at least to the status of the switches 2/3, and an antenna 6 for transmitting the status signal. According to an embodiment, the wireless transmission device 5 is a Bluetooth® chip, and may be configured for communication via Bluetooth® Low Energy Technology.

Figure 2:
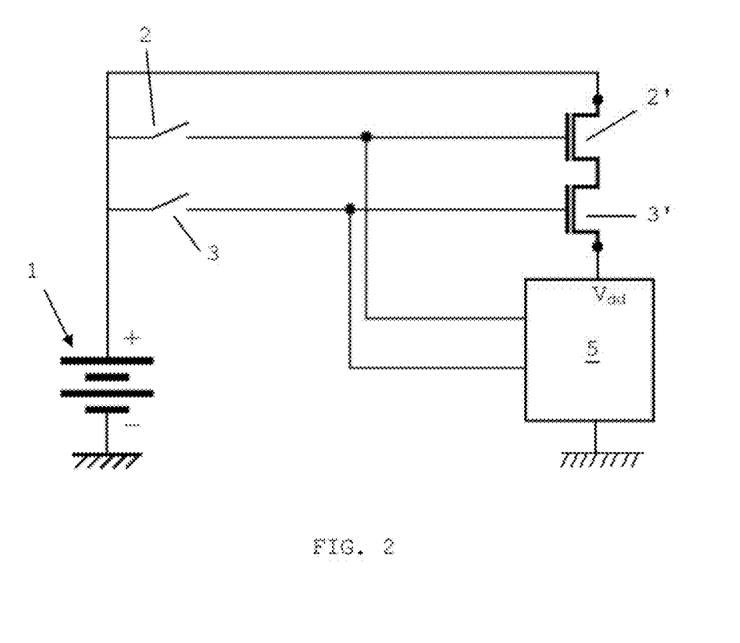
FIG. 2 illustrates the electrical circuitry in an exemplary remote control enable device.

FIG. 2 illustrates exemplary architecture of the circuitry 4. In this architecture, the Bluetooth® chip 5 is powered via the transistors 2'/3' only when both the switches 2 and 3 are closed simultaneously. The activation signal is thus an on/off signal switching the Bluetooth® chip on or off depending on whether or not both switches are closed simultaneously. When both switches are open, or one is open and one closed, the chip is not powered and therefore emits no signal. When the chip is active, it emits a signal, comprising at least the information that both switches are closed, and possibly further information. This architecture minimizes the power consumption of the RC enable device as the Bluetooth® chip consumes power only when the two switches are closed simultaneously.

As further illustrated in FIG. 1, the Bluetooth® chip 5 communicates with a receiver 7 configured to receive the status signal through its antenna 8 and pass it on to a control unit 9. This control unit 9 may also be referred to as a safety control unit because it performs safety related functions. The receiver 7 and the control unit 9 are shown separately but could be part of the same physical apparatus. The receiver 7 is equipped with a second Bluetooth chip 11 configured to transfer the received status signal unchanged to the control unit 9. The control unit 9 can be a PLC based safety control unit configured to analyse the received signal, and, depending on the outcome of the analysis, send a control signal over connection 12 towards an application module 13. Application module 13 is a software application configured to govern one or more operations of a medical apparatus (not shown) to be controlled by the actual remote control device 14, illustrated in FIG. 1. The application module 13 can be a part of the medical apparatus or in connection with said medical apparatus. The medical apparatus can be, for example, a rotating gantry used in a particle therapy facility, with the remote control device 14 controlling 3D motion of the gantry.

The remote control device 14 may be incorporated in a common housing 25 together with the RC enable device 10. The remote control device 14 commands the application module 13 via a communication channel 15, illustrated by the dotted line in FIG. 1. This communication channel 15 is a wireless communication channel that is distinct from the Bluetooth channel used between the RC enable device 10 and the receiver 7. Thus, the remote control device 14 transmits through dedicated transmission means (symbolized by the antenna 16) to dedicated receiving means (symbolized by antenna 17) connected to the application module 13.

Communications between the control unit 9 and the remote control device 14, for example to confirm that remote control is activated, can take place over the channel 15, using any commonly known method.

In the embodiment of FIG. 1, the two switches 2 and 3 are closed simultaneously for the remote control to be allowed. The signal transmitted by the RC enable device 10 must therefore at least comprise information allowing the control unit 9 to identify the state of the two switches. A number of further criteria may need to be met before the remote control is allowed. For example simultaneous actuation of the switches must be established longer than a minimum time span, and a verification of an identifier of the RC, enable device 10 may be required, when multiple RC enable devices are used in the same environment. When the switches 2/3 are not closed simultaneously or one of the additional criteria is not met, remote control of the medical apparatus is denied.

According to an embodiment, the sending of status signal from the RC enable device 10 to the receiver 7 is performed on a repetitive basis and continues on this repetitive basis after the remote control device 14 has taken control of the medical apparatus. Each repeated signal is verified by the control unit 9. As soon as the control unit 9 determines that not all of the criteria are satisfied, the connection between the remote control device 14 and the application module 13 is terminated.

Figure 3:
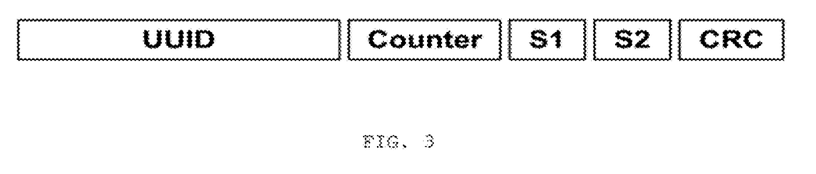
FIG. 3 shows an example of a Bluetooth® digital signal sent from a remote control enable device according to the present disclosure.

FIG. 3 shows an exemplary structure of a digital Bluetooth® status signal sent from the RC enable device 10. The signal comprises an identification sequence UUID, related to an ID code of the RC enable device 10. This is required when multiple RC enable devices are used in the same environment. A counter value is then added. The counter value is produced by a counter device that may be part of the RC enable device's circuitry 4 or part of the chip 5. The counter value is used by the control unit 9 to verify the time elapsed between various signals coming from the RC enable device 10, so that the verification procedure can be programmed to ignore signals sent with too little time in between, indicating that they are generated by inadvertent actuation of the RC enable buttons. Then two sequences S1 and S2 directly relate the status (open or closed) of the switches. Finally, a signature sequence, for example a Cyclic Redundancy Check (CRC) is added to be used for verifying certain characteristics of the signal as such.

Figure 4:
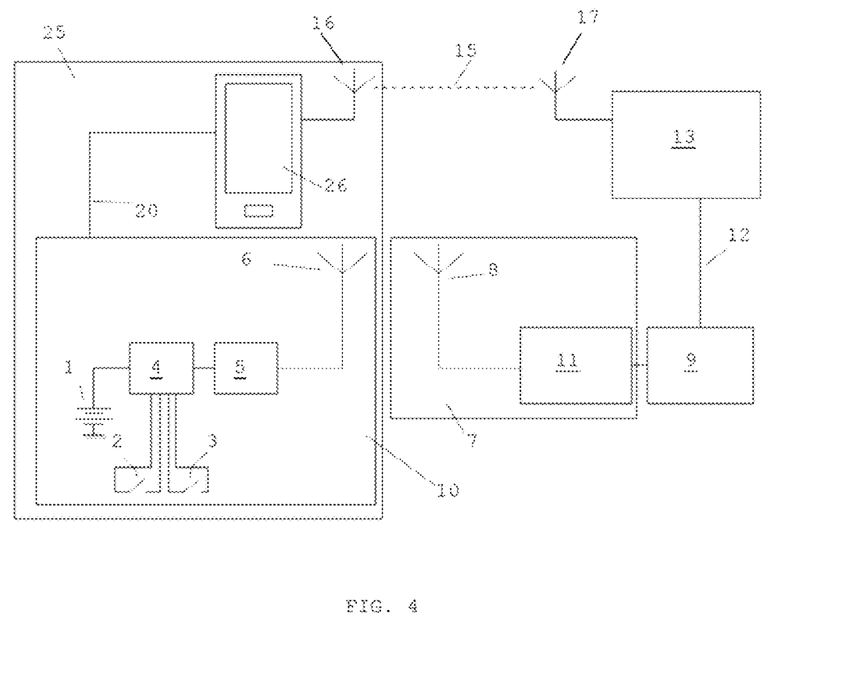
FIG. 4 illustrates an embodiment wherein the remote control device is a mobile phone.

According to an embodiment of the present disclosure as illustrated in FIG. 4, the RC enable device 10 is connected to the remote control device 14 via a physical connection 20, such as a cable between the RC enable device 10 and the remote control device 14. Through this connection 20, the remote control device 14 is capable of receiving an additional verification signal from the RC enable device 16, said signal being related to the state of the switches 2 and 3. For example, the connection 20 can transfer a signal indicating that one of the switches is open while the other is closed. In this way, and independently from the communication via the Bluetooth® channel, a signal can be sent to the control unit 9 via the remote controls communication channel 15, at which point the control unit 9 can take appropriate action.

Figure 5:
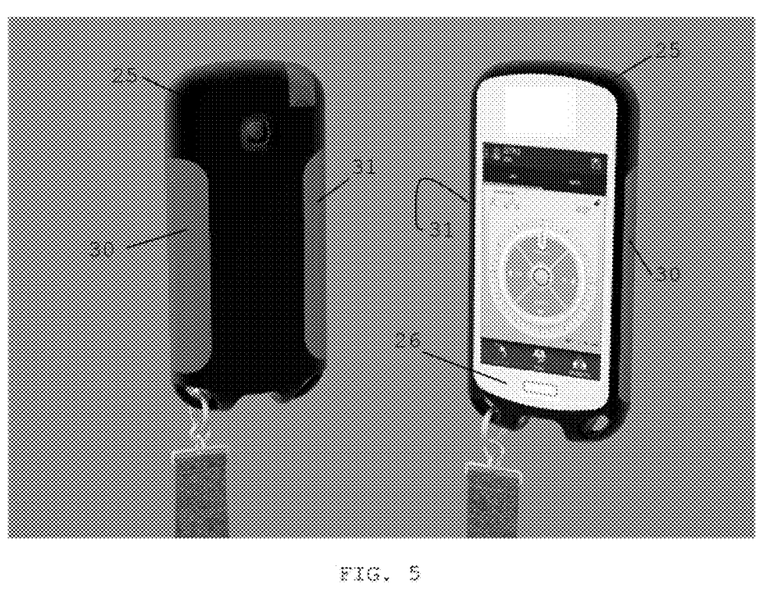
FIG. 5 illustrates an exemplary hand-held housing as shown in FIG. 4, incorporating the remote control enable device and a mobile phone acting as the remote control device.

Further in the embodiment of FIG. 4, though not necessarily in combination with the connection 20, the remote control device is a mobile phone 26, such as a smart phone that is inserted in the hand-held common housing 25. The mobile/smart phone may be removably inserted in the housing 25. FIG. 5 illustrates an exemplary design of the hand-held housing 25, with a smart phone 26 acting as the remote control device. The housing 25 may also be referred to as a hand-held pendant, which can be hung around the operators neck, for example. The housing comprises two push buttons 30/31 on either side of the housing, which can be easily gripped and actuated simultaneously by the operator. The push buttons are the enable buttons referred to above, which actuate the switches 2/3 respectively mounted inside the housing. The smart phone 26 can be inserted in the housing and removed from it. According to an embodiment, the push buttons 30/31 must be actuated continuously in order for the remote control to be effectuated. If it is present, the connection 20 between the smart phone 25 and the RC enable device 10 may be established via an ordinary microphone cable inserted via a microphone jack into the smart phone 26. The smart phone is provided with a suitable program, for example provided in the form of a downloadable app, through which the operator can control the medical apparatus 13 from a remote location, with the command signals being sent over a local Wifi® connection 15. The RC enable device 10 communicates with the control unit 9 via a Bluetooth® channel, as described above.

Figure 6:
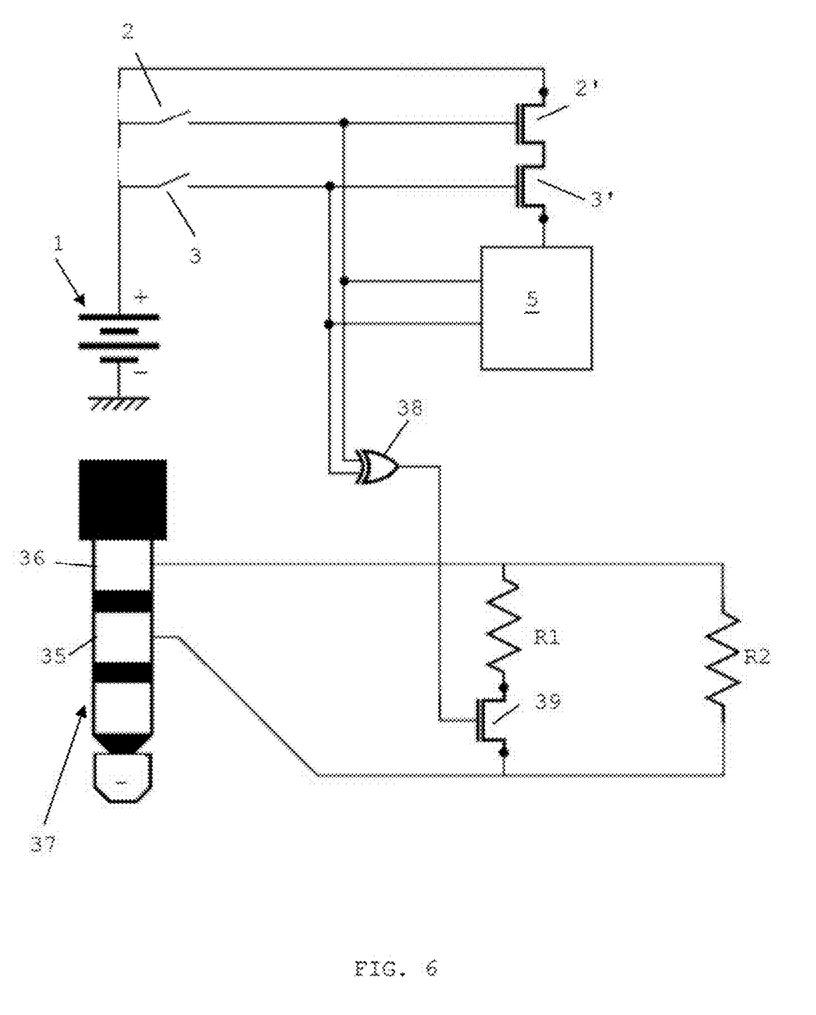
FIG. 6 illustrates an embodiment of the electrical circuitry in the exemplary remote control enable device of FIGS. 4 and 5.

FIG. 6 illustrates the circuitry 4 in the exemplary devices of FIGS. 4 and 5, and shows how circuitry 4 is connected to the ground 35 and microphone contact 36 of the jack 37 inserted in the smart phone 26. The status of the switches 2/3 is transferred to a logical exclusive OR device 38, which outputs a signal only when the switches 2 and 3 are not in the same position, i.e. when one switch is open and the other is closed. Therefore, when the switches are in the same position, either open or closed, the jack 37 receives a signal via resistor R2, whereas when one of the switches is open and the other dosed, the transistor 39 conducts and the jack receives a signal via resistor R1. The values of R1 and R2 are chosen suitably for generating distinct signals so that the status of the switches can be effectively detected. The status of the switches can be transferred to the control unit 9 through the communication channel of the remote control device, in this case through the Wifi® channel 15 of the smart phone 26 used as the remote control.

Figure 7:
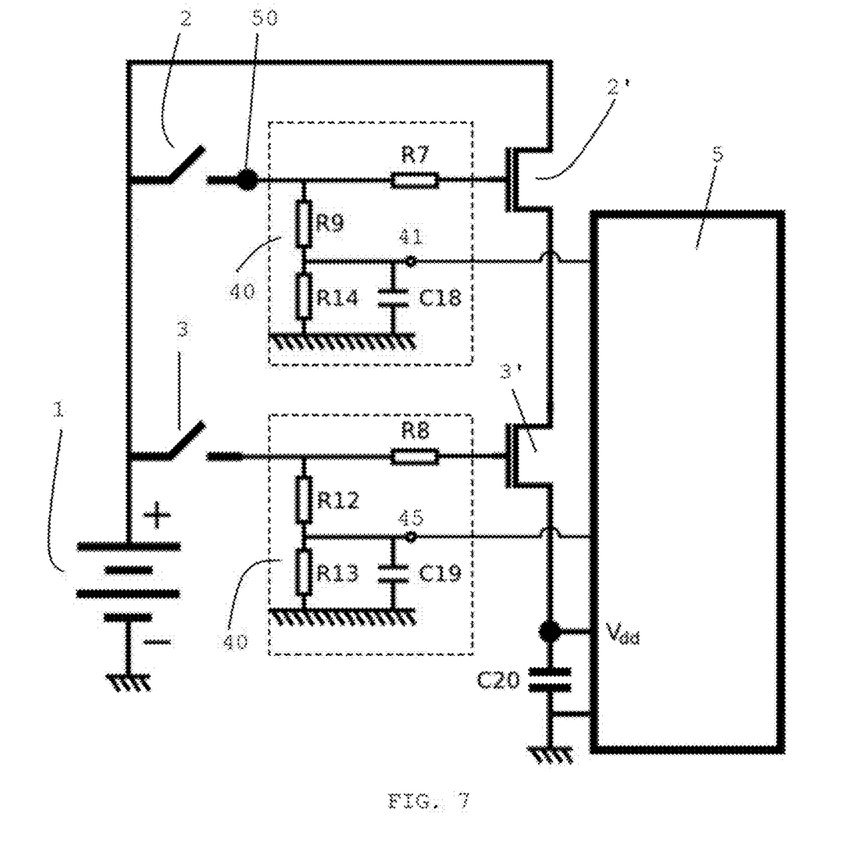
FIG. 7 shows the circuitry in an exemplary remote control enable device.
Figure 8:
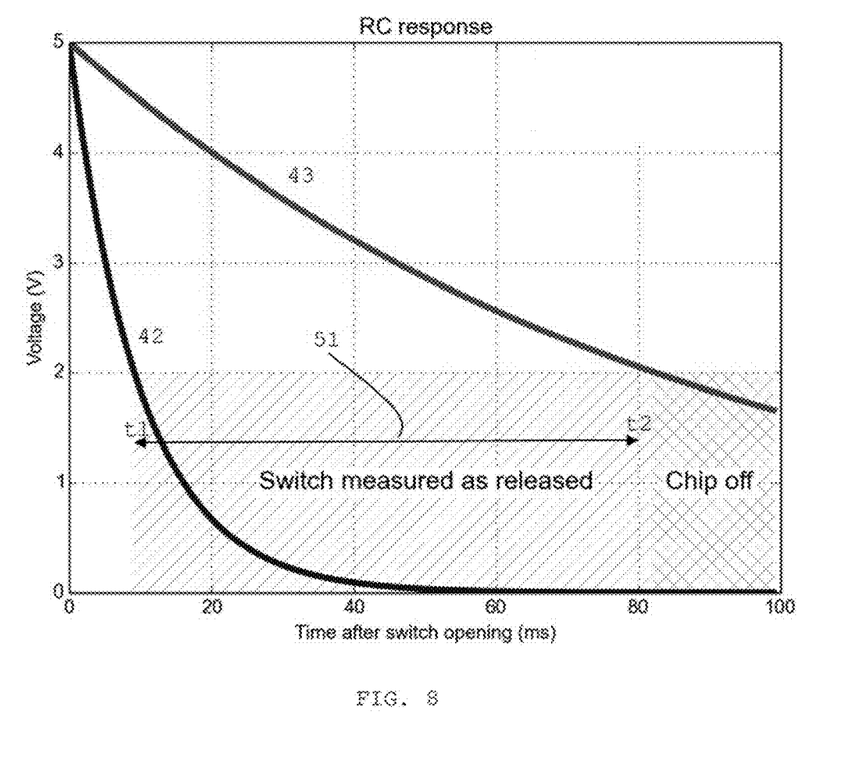
FIG. 8 illustrates characteristic voltage vs time curves upon opening switch in the circuitry of FIG. 7.

FIG. 7 shows an exemplary embodiment with an alternative configuration of the circuitry 4. In this embodiment, an RC circuit 40 is provided after each of the switches 2 and 3, and a capacitor C20 is provided in parallel with the supply pins (Vdd and ground) of the Bluetooth® (or equivalent) chip 5. The RC circuit 40 provided for switch 2 is described first. A resistive divider R9/R14 with a capacitor C18 parallel to R14 is coupled between the output terminal 50 of the switch 2 and the ground reference of the power source 1 (reference of battery 1, for example). The output terminal 41 of the RC circuit is connected as an input to the chip 5, which transmits the level of the signal appearing on terminal 41 to the receiver 7. The resistive divider tailors the signal level at terminal 41 so that it can be used as an input to the chip 5. Alternatively, if the chip 5 is capable of receiving higher signal levels, the signal at terminal 50 could be connected directly to the chip 5. The values of the capacitor C18 and the resistors R9/R14 and R7 are chosen such that upon opening the switch 2, the voltage at the output terminal 50 of the switch 2 drops to zero according to a given characteristic. This is illustrated in FIG. 8, where curve 42 represents the voltage at terminal 50, upon opening the switch 2 at t=0s. The voltage at terminal 41 decreases according to a similar curve as curve 42, but starting at a lower voltage.

The value of capacitor C20 is chosen such that the supply voltage to the chip 5 drops to zero significantly slower than the voltage at terminals 50 and 41. A suitable characteristic of the chip's supply voltage is shown as curve 43 in FIG. 8. At point t1, the voltage at terminal 50 (and hence at terminal 41) has dropped sufficiently low for the control unit 9 to conclude that the switch 2 has effectively opened. At this moment, the power supply to the chip is still sufficiently high to enable the transmission of the signal level at terminal 41. In the timeframe 51 starting from t1 to the moment t2 at which the power to the chip becomes too low to enable transmission, the chip 5 remains powered even though the switch is already open. This a consequence of the specifically chosen RC constants of the RC circuit 40 on the one hand, and of the RC circuit formed by the capacitor C20 and the chip 5. During this timeframe 51, the chip is thus capable of sending a number of signals as described in FIG. 3 to the receiver 7. The sequence S1 in this case is not one of two possible values 'open/closed', but a sequence that relates to the level of the signal at terminal 41. This level will become gradually lower in the consecutive sequences sent during the timeframe 51, as the signal at terminal 41 decreases. The sequence S1 therefore also varies within a pre-defined range of values rather than switching between an 'on/off' state. The sequences S1 sent during the timeframe 51 allow the control unit 9 to perform a check on the operation of switch 2, after the switch has effectively been opened. If the level of the signal at terminal 41 does not decrease according to a predefined characteristic and/or does not stay within the predefined range, it is concluded that the switch 2 is not operating correctly.

The RC circuit 40 (provided after the second switch 3) may have the same layout as that of the first switch 2. The signal at output terminal 45 of the second RC circuit may be equally fed as an input to the chip 5, and the values of R12/R13/R8 and C19 may equally be chosen so that the signal at terminal 45 drops according to a given curve, allowing a number of signals including S2 sequences (for example, as described in FIG. 3) to be transmitted after the switch has opened, so as to allow the checking of the correct functioning of the switch 3 in the manner described above. The values of R12/R13/R8 and C19 may be chosen so that the range within which the S2 sequences must be situated differs from or partially overlaps with the range defined for the S1 sequences.

When both switches are opened simultaneously or within a timespan significantly smaller than the timeframe 51, the above-described check procedure can be performed for both switches. In practice, however, one switch may be opened before the other with a time difference larger than the timeframe 51, due to the manual release of the push buttons which are actuating the switches 2/3. The switch that is opened last may not be checked given that the power to the chip is already cut by the time the switch opens. Statistically, however, the probability that the same switch always opens first is small. Further safety features may be built in by monitoring the time between consecutive instances t1 at which each of the switches is effectively detected as opening. If an excessively long time elapses between two such instances for one of the switches, this may mean that the switch has remained effectively closed during this time and is thus malfunctioning.

The embodiment of FIG. 7 thereby allows checking the correct functioning of the switches without requiring a communication over the remote control communication channel 15. In contrast, in the embodiment illustrated in FIG. 6 the jack connection of the smart phone 26 is used for communicating the status of the switches over the wireless channel 15.

The presence of the RC circuits 40 allows adequate tuning of the RC constant and hence the shape of the curve 42 in FIG. 8, i.e. the delay by which the voltage at terminal 50 drops to zero. However, one or both circuits 40 may be omitted (as in FIG. 2), as long as the capacitor C20 or any equivalent circuit ensures that the chip's supply voltage drops sufficiently slowly to allow transmission of the status signal S1/S2 for each switch during a timespan after the switch has effectively been opened. When the circuits 40 are absent, the curve 42 will drop much faster and may be difficult to detect gradually decreasing values of the signal at terminals 41 and 45. The sequence S1/S2 can in that case not be defined as lying within a range of values but will be an 'on/off' value as in the case of FIG. 2. Nevertheless, due to the capacitor C20, status signals S1/S2 are transmitted after opening the switch, which does allow a check of the adequate functioning of the switch. A delay circuit such as circuit 40 described herein may also be applied without the capacitor C20 or equivalent circuit, such as in a circuit as shown in FIG. 2, for example to ensure that the signal level appearing at the inputs of the chip 5 is compatible with the operation of said chip.

The layout of the RC circuits 40 is not limited to those shown in FIG. 7. The circuits also have a filtering function, in that they filter out oscillations of the switches 2 and 3. However, any circuit layout may be used that defines a more delayed drop to zero of the voltage at terminal 50 compared to the case where no circuit is applied. The RC circuits 40 may therefore be more generally referred to as 'delay circuits'. The capacitor C20 can be replaced by any suitable circuit that performs the same function of regulating the supply voltage drop in the manner described above.

Figure 9:
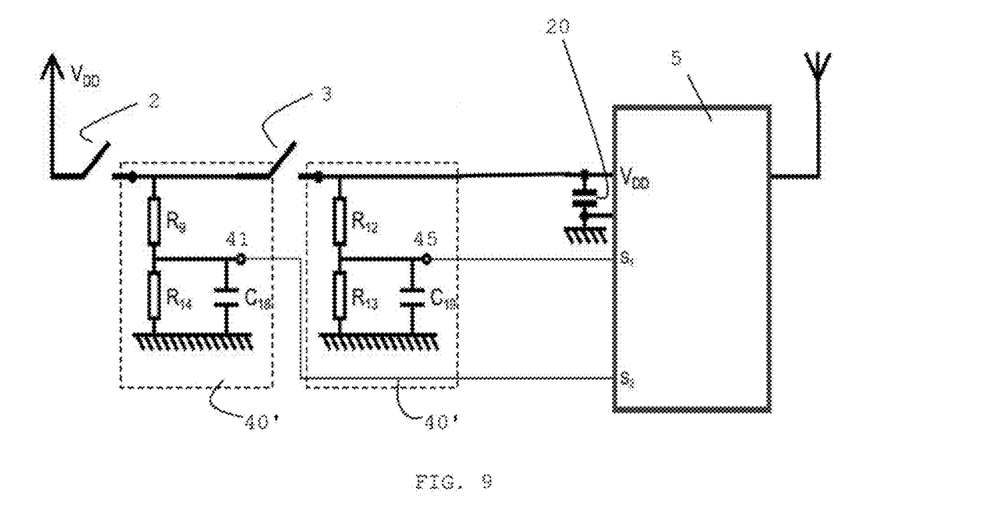
FIG. 9 shows an exemplary alternative to the circuit of FIG. 7.

FIG. 9 shows an exemplary alternative to the circuit of FIG. 7, wherein the switches 2 and 3 are arranged in series. The same RC circuits are provided for each switch. Further, the capacitor C20 is provided in parallel with the supply pins (Vdd and ground) of the Bluetooth® (or equivalent) chip 5. The same functionality as the parallel version is obtained. The delay circuits 40' establish a controlled drop to zero of the voltages at terminals 41 and 45 when the respective switches 2 and 3 are opened. The capacitor ensures a slow drop to zero of the chip's supply voltage, slower than the drop to zero at terminals 41/45, to thereby allow transmission of the status of the switch after the switch is opened. This circuit may be less technically complex by avoiding the implementation of the transistors 2' and 3'.

Figure 10:
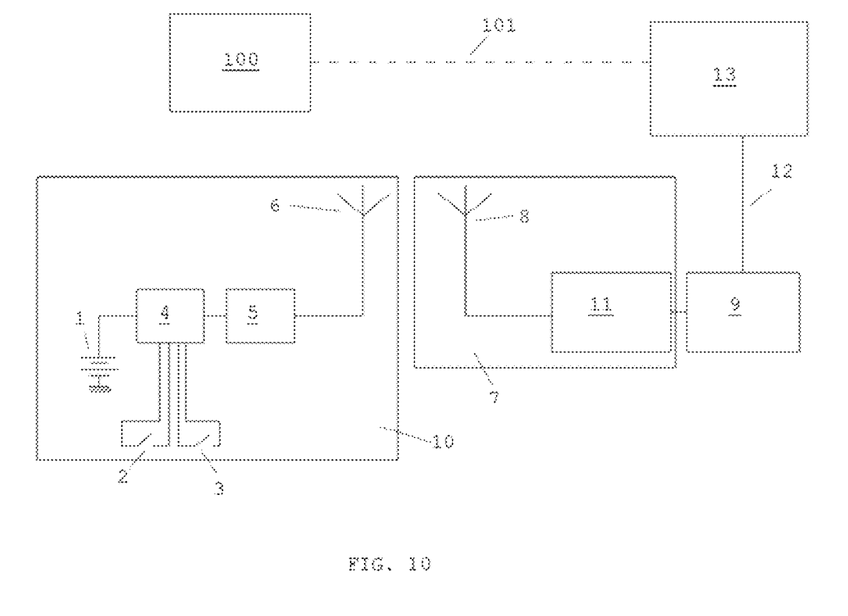
FIG. 10 illustrates an exemplary apparatus according to another embodiment of the present disclosure

According to an embodiment, a control apparatus equipped with the circuitry 4 executed according to the embodiment of FIG. 7, with or without the RC circuits 40 or equivalent delay circuits, i.e. with at least the capacitor C20 or an equivalent component to maintain an effective supply voltage to the chip 5 during a sufficiently long timeframe, but wherein the remote control enable device 10 is not incorporated in a common hand-held housing together with a wireless remote control device. The above description with reference to FIGS. 7 and 8 is applicable in its entirety to this embodiment. The RC enable device applicable in this embodiment can be used with any type of remote control, either wireless or wired. The RC enable device of this embodiment is provided with suitable buttons for actuating the one or more switches 2/3. FIG. 10 shows an exemplary apparatus according to this embodiment. The remote control device 100 is this embodiment can be any suitable type of remote control device, wireless or not, and the communication channel 101 by which said device communicates with the application module 13 can be any type of channel. Apart from these differences, relevant portions of the above described embodiments that are not linked to the common hand-held housing are applicable here. The present disclosure is also related to a remote control enable device.

In an embodiment, the present disclosure relates to a remote motion enable system for remotely generating a motion enable state to enabe operations of a medical apparatus or operations of components of a medical apparatus. This system comprises a remote control enable device 10 as described herein, comprising one or more manually operable switches 2/3, a power source 1 and circuitry 4 configured to generate, for each of the one or more switches, a corresponding switch status signal when the switch is closed and a wireless transmitter 5 linked with the circuitry 4. In the remote motion enable system, the transmitter 5 is configured to periodically transmit a data package wirelessly, such as the data package illustrated in FIG. 3. The data package may comprise a number of parameters. For example, the data package transmitted comprises at least the switch status signal of each of the one or more switches.

The system may further comprises a receiving device 7 configured to receive the data package transmitted from the transmitter and a safety control unit 9 coupled to the receiving device 7 through a transmission line for receiving the data package. This safety control unit 9 comprises an algorithm configured to periodically verify the data package or part of the data package and to generate a motion enable state only when the switch status signal of each of the one or more switches is within a predefined range and to disable the motion enable state when no switch status signal or no signal within the predefined range is received within a timeout period. The predefined range can be a range that is stored in the memory of the safety control unit 9. The timeout period is a period that also can be stored in a memory table or be part of the software code of the safety controller. By using this timeout, when the user stops activating the switches, for example in the case of an emergency, the safety control unit 9 will detect this because no switch status signal within the pre-defined range is received after the timeout period.

When the motion enable state is disabled, the medical device or a component of the medical device cannot be operated. Typically a patient positioner or a gantry cannot be moved anymore. The motion enable state can for example be a voltage level and when the motion state is disabled, the voltage drops to zero level. The motion enable state is transmitted over a connection 12 towards an application module 13 which may be a controller configured to govern one or more operations of a medical apparatus or a component of a medical apparatus. When for example the motion enable state changes from the enable state (e.g. a +24 V signal) to a disable state (e.g. 0 V), the operations of the medical apparatus or a component of a medical device are prohibited or stopped when the medical apparatus or component of the medical apparatus was in operation. This functioning of the remote enable system may be independent of the functioning of, for example, a remote control device 14 that transmits operating instructions to the medical device or a component of the medical device. The remote control device 14 may thus not be a part of the remote motion enable system. In some embodiments, when the remote control device 14 is incorporated together with the remote control enable device 10 in the same hand-held housing, the remote motion enable system with its remote control enable device 10 still operates functionally independently from the remote control device 14.

The data package transmitted from the transmitter 5 to the receiving device 7 may comprise an identifier identifying the remote control enable device transmitting the data, wherein the control system verifies that the received identifier matches a reference identifier and wherein the matching with the reference identifier is a condition to generate the motion enable state.

In some embodiments, the transmitter 5 and the receiving device 7 operate through a Bluetooth communication protocol configured for low power consumption.

In some embodiments, the remote control enable device incorporated into a hand-held housing configured for housing the one or more switches 2/3, the power source 1, the circuitry 4 and the wireless transmitter 5.

In some embodiments, the receiving device 7 is configured to receive data from only one transmitter at a time.

While the present disclosure is illustrated and described in detail according to the above embodiments, the present disclosure is not limited to these embodiments and additional embodiments may be implemented. Further, other embodiments and various modifications will be apparent to those skilled in the art from consideration of the specification and practice of one or more embodiments disclosed herein, without departing from the scope of the present disclosure.

The invention claimed is:

1. A system for controlling a medical apparatus, comprising:
    a housing configured to be handheld, the housing including:
        a remote control device configured to control the medical apparatus over a first wireless communication channel; and
        a remote control enable device that further includes:
            one or more switches;
            a wireless transmitter configured to transmit, over a second wireless communication channel, a status signal associated with the status of the one or more switches; and
            one or more buttons configured to operate the one or more switches;
    a receiving device, external to the housing and configured to receive the status signal; and
    a control unit, coupled to the receiving device, configured to enable control of one or more operations of the medical apparatus based on the status signal, wherein the control unit enables control when the status signal indicates the one or more switches are closed.

2. The system according to claim 1, wherein the remote control enable device comprises a power source and a circuit configured to power the wireless transmitter only when the one or more switches are closed.

3. The system according to claim 2, wherein the circuit is configured to maintain a power supply to the wireless transmitter sufficient for enabling transmission, during a timeframe after opening the one or more switches, of one or more status signals, and wherein the control unit is configured to determine whether the one or more opened switches are functioning correctly based on the status signals transmitted during the timeframe.

4. The system according to claim 3, wherein:
    the wireless transmitter is a wireless communication chip comprising one or more power supply pins; and
    the circuit comprises a capacitor coupled between the one or more power supply pins.

5. The system according to claim 2, wherein the circuit comprises a delay circuit coupled to at least one of the one or more switches, wherein the delay circuit is configured to force an output terminal of the one or more switches to zero when the one or more switches are opened.

6. The system according to claim 1, wherein:
    the remote control enable device further comprises a circuit configured to:
        detect information on the status of the one or more switches; and
        transmit the information through a cable to the remote control device; and
            wherein the remote control device is configured to:
                communicate the information to the control unit through the first wireless communication channel.

7. The system according to claim 6, wherein the remote control enable device comprises two switches, and wherein the information on the status of the switches indicates whether one switch is open while the other switch is closed.

8. The system according to claim 1, wherein the housing is configured to removably receive at least one of the remote control enable device or the remote control device.

9. The system according to claim 1, wherein the remote control device comprises a mobile phone configured to enable control of the medical apparatus.

10. The system according to claim 1, further comprising:
    a hand-held device, wherein the handheld device includes:
        the housing;
        the remote control enable device; and
        the remote control device.

11. A method for controlling a medical apparatus by the system according to claim 1, the method comprising:
    closing the one or more switches on the remote control enable device;
    sending, by the remote control enable device, the status signal to the receiving device;
    communicating, by the receiving device, the status signal to the control unit,
        wherein the status signal is associated with at least the status of the one or more switches;
    determining that the status signal meets one or more criteria, wherein the one or more criteria indicates whether the one or more switches are closed;
    enabling, by the control unit, an operator to control the operation of the medical apparatus based on the determination; and
    operating the medical apparatus using the remote control device.

12. A system for controlling one or more operations of a medical apparatus, comprising:
    a housing configured to be handheld, the housing including:
        a remote control device configured to control the one or more operations of the medical apparatus over a first communication channel;
        a remote control enable device that further includes:
            one or more switches;
            a wireless transmitter configured to transmit, through a second wireless communication channel, a status signal associated with the status of the one or more switches; and
            a circuitry configured to power the wireless transmitter when the one or more switches are closed, wherein the circuitry is configured to maintain power to the wireless transmitter sufficient for enabling transmission, during a timeframe after opening the one or more switches, of the status signal during the timeframe;
    a receiving device, external to the housing and configured to receive the status signal; and
    a control unit, coupled to the receiving device, configured to:
        enable control of the one or more operations of the medical apparatus based on the status signal, wherein the control unit enables control when the status signal indicates the one or more switches are closed; and
        determine a functional status of the one or more opened switches based on the status signal transmitted during the timeframe.

13. The system according to claim 12, wherein:
    the wireless transmitter is a wireless communication chip comprising one or more power supply pins; and the circuit comprises a capacitor coupled between the one or more power supply pins.

14. The system according to claim 13, wherein the circuit further comprises a delay circuit coupled to at least one of the one or more switches, wherein the delay circuit is configured to force an output terminal of the one or more switches to zero when the one or more switches are opened.

15. A remote motion enable system to remotely enable one or more operations of a medical apparatus, comprising:
a housing configured to be handheld, the housing including:
  a remote control device configured to control the medical apparatus over a first wireless communication channel;
  a remote control enable device that further includes:
    one or more switches;
    a power source and circuitry configured to generate a switch status signal for each of the one or more switches when the one or more switches are closed; and
    a wireless transmitter coupled with the circuitry and configured to periodically transmit a data package, over a second wireless communication channel, when the one or more switches are closed, wherein the data package comprises at least the switch status signal of each of the one or more switches;
a receiving device external to the housing and configured to periodically receive the transmitted data package; and
a safety control unit, coupled to the receiving device, configured to receive the data package, wherein the safety control unit comprises an algorithm configured to:
  periodically verify at least part of the data package;
  generate a motion enable state when the switch status signal of each of the one or more switches is within a predefined range; and
  disable the motion enable state when the switch status signal is not received within a timeout period.

16. The remote motion enable system according to claim 15, wherein the data package comprises an identifier identifying the remote control enable device transmitting the data package, and wherein the safety control system is configured to periodically verify at least part of the data package to generate the motion enable state when the received identifier matches a reference identifier.

17. The remote motion enable system according to claim 15, wherein the transmitter and the receiving device operate over a Bluetooth communication protocol.

18. The remote motion enable system according to claim 15, further comprising:
a housing configured to be handheld, the housing including:
  the remote control enable device;
  the one or more switches;
  the power source;
  the circuitry; and
  the wireless transmitter.

19. The remote motion enable system according to claim 15, wherein the receiving device is configured to receive data from only one transmitter at a time.

* * * * *